United States Patent [19]

Ranke et al.

[11] 4,324,567
[45] Apr. 13, 1982

[54] SEPARATION OF GASEOUS COMPONENTS FROM A GASEOUS MIXTURE BY PHYSICAL SCRUBBING

[75] Inventors: Gerhard Ranke, Poecking; Horst Weiss, Munich, both of Fed. Rep. of Germany

[73] Assignee: Linde Aktiengesellschaft, Wiesbaden, Fed. Rep. of Germany

[21] Appl. No.: 107,119

[22] Filed: Dec. 26, 1979

[30] Foreign Application Priority Data

Dec. 23, 1978 [DE] Fed. Rep. of Germany ....... 2856078

[51] Int. Cl.³ .............................................. B01D 53/14
[52] U.S. Cl. ........................................ 55/43; 55/46; 55/51; 55/73
[58] Field of Search ................... 55/48, 68, 73, 53, 51, 55/46, 43, 223

[56] References Cited

U.S. PATENT DOCUMENTS

| | | | |
|---|---|---|---|
| 3,193,986 | 7/1965 | Förster | 55/43 |
| 3,590,555 | 7/1971 | Wackernagel | 55/51 |
| 3,640,052 | 2/1972 | Konoki et al. | 55/48 |
| 3,659,401 | 5/1972 | Giammarco | 55/43 |
| 3,975,172 | 8/1976 | Ranke | 55/51 |
| 4,050,909 | 9/1977 | Ranke | 55/48 |

*Primary Examiner*—John Adee

*Attorney, Agent, or Firm*—Millen & White

[57] ABSTRACT

In a process for separating and obtaining as product gases at least two gaseous components from a gaseous mixture containing same by scrubbing with a physical scrubbing liquid exhibiting a higher dissolving power for at least one of the components to be separated than for at least one other of these components, wherein a first scrubbing liquid stream, loaded with all of the components to be separated, and a second scrubbing liquid stream, merely containing proportions of the less soluble component or components, are withdrawn from the scrubbing stage; a gaseous fraction is liberated by expansion of the first scrubbing liquid stream, freed of the more soluble component or components by treatment with the second, likewise expanded scrubbing liquid stream and withdrawn as a first product stream; and the scrubbing liquid streams are finally subjected to a separation of the more soluble components as well as of residual proportions of the less soluble components, thus obtaining a second product gas, the improvement which comprises further expanding the scrubbing liquid streams to obtain a gaseous fraction prior to the separation serving for obtaining the second product gas, recompressing the thus-liberated, gaseous fraction and scrubbing the recompressed gaseous fraction with the second scrubbing liquid stream.

11 Claims, 2 Drawing Figures

SEPARATION OF GASEOUS COMPONENTS FROM A GASEOUS MIXTURE BY PHYSICAL SCRUBBING

BACKGROUND OF THE INVENTION

This invention relates to a process for the separation and obtaining at least two gaseous components from a gaseous mixture containing same, by scrubbing with a physical scrubbing liquid, i.e., a liquid which can absorb gases without any chemical reaction, e.g., methanol.

Such processes are known from German Pat. No. 1,814,064, as well as DAS [German Published Application] No. 2,548,700, English language equivalents being U.S. Pat. Nos. 3,718,006 and 4,050,909, respectively.

German Pat. No. 1,814,064 relates specifically to the removal of carbon dioxide and hydrogen sulfide from a hydrogen-rich raw gas. This raw gas is treated in a two-stage scrubbing step: the first stage comprises scrubbing the raw gas countercurrently with carbon dioxide-loaded-methanol to scrub out hydrogen sulfide; and the second stage comprises scrubbing the resultant treated raw gas with completely regenerated methanol to scrub out carbon dioxide. A portion of the methanol loaded with carbon dioxide in the second scrubbing stage is withdrawn therefrom and introduced to the first scrubbing stage and, after absorption of the hydrogen sulfide, withdrawn as a first scrubbing liquid stream. The remaining portion of the methanol discharged from the second scrubbing stage and loaded with carbon dioxide but essentially no hydrogen sulfide is discharged from the scrubbing unit as a second stream of scrubbing liquid.

The first scrubbing liquid stream is expanded, with liberation of a gaseous fraction containing carbon dioxide and hydrogen sulfide. This gaseous fraction is then freed of hydrogen sulfide by countercurrent scrubbing with the likewise expanded, second scrubbing liquid stream. (This hydrogen sulfide represents the component more soluble in methanol as compared with the carbon dioxide.) Thus, this treatment results in a first product gas stream containing primarily carbon dioxide which, however, is greatly contaminated with nitrogen since the first scrubbing liquid stream, after expansion and liberation of the gaseous fraction, is additionally stripped with a gaseous nitrogen stream. The stripping gas stream, after absorbing the additionally liberated components, is likewise subjected to the treatment with the second scrubbing liquid stream, to rewash any concomitantly stripped-out hydrogen sulfide. The two methanol-scrubbing liquid streams are finally combined and fed to a warm regeneration stage effecting the removal and production of the second product gas comprising hydrogen sulfide as well as residual carbon dioxide.

Although a gaseous product fraction enriched in hydrogen sulfide can be obtained with the aid of this conventional process, the degree of recovery of carbon dioxide is extremely poor. It would on the one hand be possible for the gaseous carbon dioxide fraction liberated during the expansion of the second scrubbing liquid stream (methanol preliminarily loaded with carbon dioxide) to be obtained separately, in contrast to the process as depicted in FIG. 1 of German Pat. No. 1,814,064, where it is recovered in a mixture with stripping gas. On the other hand, however, the carbon dioxide fraction liberated during the expansion of the second scrubbing liquid stream (methanol loaded with carbon dioxide and hydrogen sulfide) will in any event be contaminated with stripping gas in the conventional process. Besides, there are still relatively high carbon dioxide proportions in the second product gas fraction comprised of hydrogen sulfide and residual carbon dioxide. Thus, the process of German Pat. No. 1,814,064 would be benefitted by an increased concentration of the hydrogen sulfide in the second product gas as well as in a maximally complete recovery of the carbon dioxide.

The second process, as shown in DAS No. 2,548,700, though more comprehensive by the incorporation of additional process steps, is not a complete answer to the desired objectives. These process steps provide a system wherein the carbon dioxide fraction liberated during the expansion of the second scrubbing liquid stream, the latter being merely preliminarily loaded with carbon dioxide, is not mixed with stripping gas, and that the treatment of the gaseous fraction, liberated during the expansion of the first scrubbing liquid stream containing carbon dioxide and hydrogen sulfide, on the one hand, and the subsequent stripping of the two scrubbing liquid streams, on the other hand, are conducted in two separate columns. Consequently, only the carbon dioxide fraction liberated during stripping is contaminated with stripping gas, while the carbon dioxide converted into the gaseous phase during the expansion of the first scrubbing liquid stream is obtained in an almost pure form. In spite of this measure, the proportion of carbon dioxide obtained in the almost pure form is only about 72%, whereas about 24% is blown off together with the stripping gas and about 4% remains in the concentrated hydrogen sulfide product fraction.

SUMMARY OF THE INVENTION

An object of this invention is to provide a further improvement in a process of the type described which leads to a higher recovery of the components to be separated, and preferably wherein the process is also conducted under economically optimum conditions.

Upon further study of the specification and appended claims, futher objects and advantages of this invention will become apparent to those skilled in the art.

To attain these objects, there is provided a process for separating and obtaining as product gas at least two gaseous components from a gaseous mixture containing same by scrubbing with a physical scrubbing liquid exhibiting a higher dissolving power for at least one of the components to be separated than for at least one other of these components, wherein a first scrubbing liquid stream, loaded with all of the components to be separated, and a second scrubbing liquid stream, merely containing proportions of the less soluble component or components, are withdrawn from the scrubbing stage; a gaseous fraction is liberated by expansion of the first scrubbing liquid stream, freed of the more soluble component or components by treatment with the second, likewise expanded scrubbing liquid stream, and withdrawn as a first product gas; and the scrubbing liquid streams are finally subjected to a separation of the more soluble components as well as of residual proportions of the less soluble components, thus obtaining a second product gas, the improvement which comprises further expanding the scrubbing liquid streams to obtain a gaseous fraction prior to the separation serving for obtaining the second product gas, recompressing the thus-liberated, gaseous fraction and scrubbing the recompressed gaseous fraction with the second scrubbing liquid stream.

These steps lead to a considerable improvement in the product gas yield, with respect to the recovery of the separated, less soluble components, specifically carbon dioxide in case of the aforementioned conventional processes. In addition, a substantial improvement is achieved with respect to the concentration of the more soluble components (hydrogen sulfide in the case of the two conventional processes) in the second product gas. The further expansion of the scrubbing liquid streams leads to the degasification of additional portions of the separated components, predominantly of the less soluble ones, but to a certain proportion also of the more soluble components. The latter are rewashed during the treatment of the liberated gaseous fraction with the second scrubbing liquid stream. Consequently, the yield is increased with regard to the production of the less soluble components, and at the same time a concentration of the more soluble components is attained in the scrubbing liquid. The liberation of the gaseous fraction, effected by the further expansion, leads to a cooling down of the scrubbing liquid; thus, in a thermodynamically favorable way, a portion of the heat of solution produced in the scrubbing column is again removed from the scrubbing liquid. The initial investment as well as the operating expenses required for the recompression of the gaseous fraction are more than compensated for by the increased product yield.

In a further development of the invention, provision is made that the scrubbing liquid streams, prior to further expansion, are subjected to an intermediate expansion and recompression. Also, this intermediate expansion leads to the liberation of a gaseous fraction containing the less soluble components predominantly. In conjunction therewith, a further concentration of the more soluble components occurs in the scrubbing liquid. The gaseous fraction liberated during the intermediate expansion is suitably recompressed and likewise subjected to treatment with the second scrubbing liquid stream. This leads to an additional increase in yield with respect to the less soluble component.

The intermediate expansion of the scrubbing liquid stream results in a cooling thereof, primarily due to the fraction which passes over into the gaseous phase during this step. The provided recompression of the scrubbing liquid streams leads, in contrast thereto, merely to a minor heating-up effect, since only the liquid phase is compressed. Therefore, provision is made to heat the scrubbing liquid streams after intermediate expansion and recompression. This is suitably accomplished countercurrently to regenerated scrubbing liquid which has been preliminarily loaded in the scrubbing column thereby being heated by the heat of absorption. The heating step of the scrubbing liquid streams after intermediate expansion and recompression leads to a further degasification of dissolved components. In this connection, it is suitable, just as in the cases dealt with above, to subject the gaseous fraction liberated during the heating step likewise to the treatment with the second scrubbing liquid stream.

Consequently, due to the treatment of three additional gaseous fractions with the second scrubbing liquid stream, as provided by this invention, a considerable increase in yield with regard to the less soluble components is attained as compared with the conventional process. This effect is obtained even without having to make use under all circumstances of a stripping gas, as must be done, for example, in the process of German Pat. No. 1,814,064.

The product gas yield as well as the concentration of the more soluble components in the second product gas can, however, be still further increased if the scrubbing liquid streams, further expanded according to this invention, are stripped with an inert gas. In this connection, here again the stripping gas loaded with thus-liberated gaseous components is to be treated with a likewise expanded partial stream branched off from the second scrubbing liquid stream, and the stripped scrubbing liquid streams are to be subsequently conducted to the separating stage which generates the second product gas. It is especially advantageous to effect this stripping step only after the expansion of the scrubbing liquid streams according to the invention and after the optionally preceding intermediate expansion and subsequent reheating steps. For, in such a case, the amount of the gaseous fraction now being liberated during the stripping step, which fraction is unavoidably contaminated with stripping gas, is considerably lower than in the conventional processes. The losses of the less soluble components to be discharged into the residual gas can thus be reduced. If the aforementioned intermediate expansion of the scrubbing liquid streams is carried out, then provision is made to combine the expanded partial stream utilized for the treatment of the loaded stripping gas, after the aforementioned treatment with the intermediately expanded, not yet recompressed scrubbing liquid streams. Accordingly, the partial stream used for the treatment of the loaded stripping gas can also be subjected to the further expansion as well as optionally to the aforementioned heating step, during which procedure, additional gaseous proportions are liberated.

Since the partial stream must be expanded prior to the treatment of the loaded stripping gas, certain proportions will also pass over from the liquid phase into the gaseous phase during this step. In this connection, provision is made also to recompress the gaseous fraction liberated during the expansion of the partial stream and subject same to the treatment with the second scrubbing liquid stream. This step helps to maximize the desired recovery of the less soluble components.

Furthermore, the invention offers the possibility of adjusting in a simple way the desired ratio of concentration of the more soluble components to the less soluble components in the second product gas. This can be done by affecting the final pressure of the further expansion of the scrubbing liquid streams in an appropriate way. If the gaseous fraction liberated during the further expansion is recompressed with the use of a compressor, as will generally be advantageous, then the final pressure of the further expansion can thus be affected by controlling the intake pressure of the compressor. This measure has an effect, above all, on the degree of degasification of the less soluble components, whereby the concentration ratio in the second product gas can be varied within wide limits.

BRIEF DESCRIPTION OF THE DRAWINGS

The figures relate to the separation and production of carbon dioxide as well as hydrogen sulfide and carbonyl sulfide from a raw hydrogen mixture. In particular.

DETAILED DESCRIPTION OF THE DRAWINGS

Figure 1:
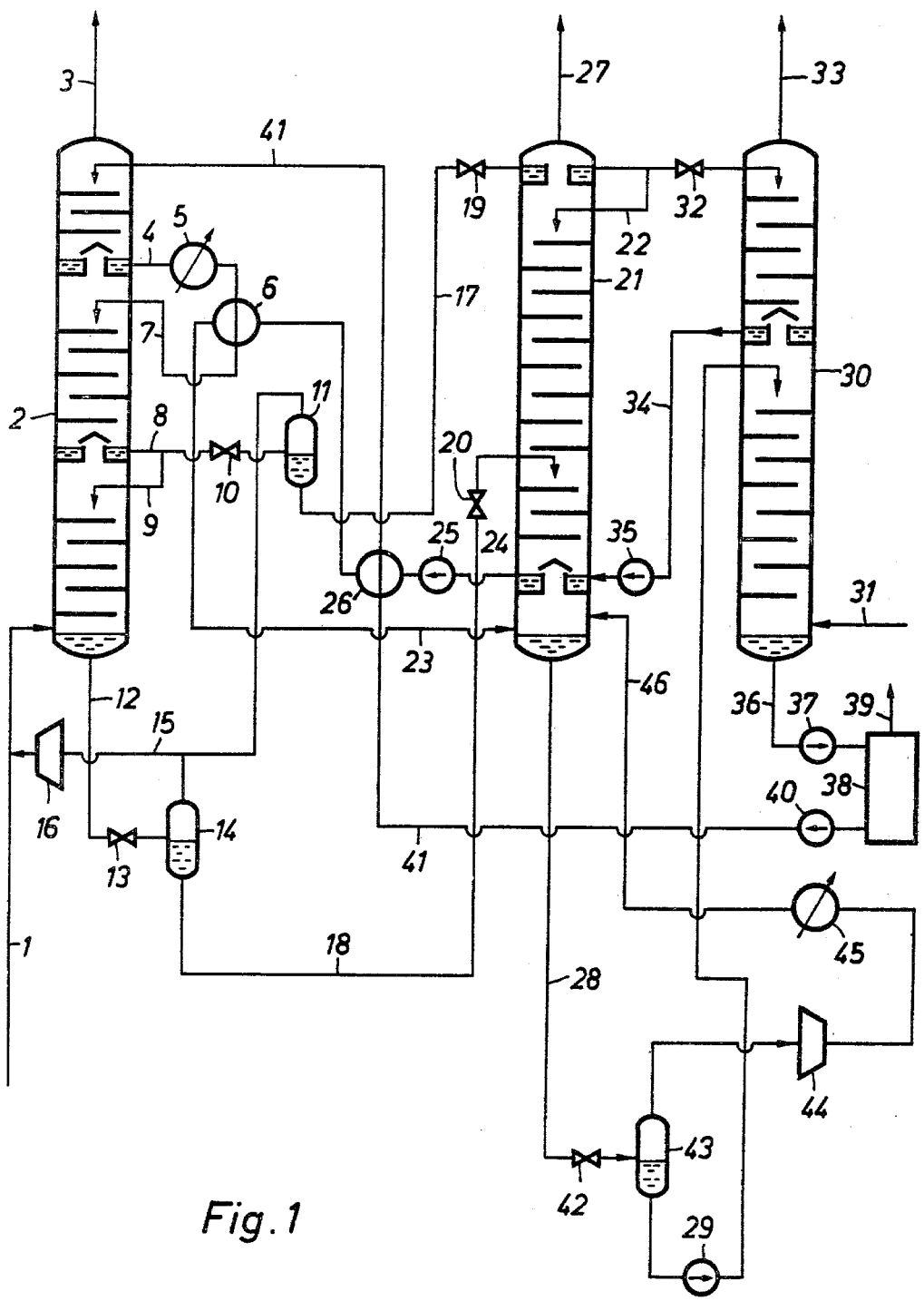
FIG. 1 shows a schematic flowsheet of a process embodying the primary aspect of the invention.

According to FIG. 1, 100,000 Nm$^3$/h. of a raw hydrogen mixture is introduced via a conduit 1; this mixture contains 69,926 Nm$^3$/h. of hydrogen, 26,548 Nm$^3$/h. of carbon dioxide, 1,717 Nm$^3$/h. of carbon monoxide, argon and methane, 1,182 Nm$^3$/h. of nitrogen, as well as 627 Nm$^3$/h. of hydrogen sulfide and carbonyl sulfide. This gaseous mixture, after having been combined with 957 Nm$^3$/h. of a compressed recycle gas, passes at a pressure of 75 bar into a scrubbing column 2. In the latter, the mixture is substantially freed of carbon dioxide, hydrogen sulfide, and carbonyl sulfide with the aid of a scrubbing liquid, so that a gaseous mixture highly enriched with hydrogen is withdrawn overhead via a conduit 3 in an amount of 72,514 Nm$^3$/h.; this gaseous mixture now contains 69,677 Nm$^3$/h. of hydrogen, 1,668 Nm$^3$/h. of carbon monoxide, argon, and methane, as well as 1,169 Nm$^3$/h. of nitrogen.

Via a conduit 41, 100 tons/hour of regenerated methanol having a temperature of 223 K is introduced to the head of the column as the scrubbing liquid. This scrubbing methanol absorbs carbon dioxide in the upper part of the column and is warmed up during this step. To remove the heat of absorption, the methanol is withdrawn via a conduit 4, and cooled in a cooler 5 with external cold and in a subsequent cooler 6 countercurrently to colder scrubbing methanol. Thereafter the methanol is returned via a conduit 7 into the middle section of the column and finally, almost saturated with carbon dioxide, withdrawn via a conduit 8. A portion of this scrubbing methanol preliminarily loaded with carbon dioxide, namely 45 t./h., is introduced via a conduit 9 into the lower section of the column and absorbs therein all of the proportions of hydrogen sulfide and carbonyl sulfide contained in the raw gas mixture. From the sump of the column, wherein a temperature is ambient of 266 K, 45 t./h. of a loaded scrubbing methanol is withdrawn via a conduit 12, this loaded scrubbing methanol entraining, in total, 14,479 Nm$^3$/h. of dissolved gases, i.e., carbon dioxide, hydrogen sulfide, and carbonyl sulfide.

The scrubbing methanol discharged from the sump of column 2 is thereafter expanded in an expansion valve 13 to a pressure of 25 bar, thus degasifying hydrogen, in particular. The gaseous components are separated in a separator 14 and conducted via conduit 15 to a compressor 16 wherein they are recompressed to the initial pressure of 75 bar, and then combined with the raw gas mixture. Scrubbing methanol loaded with carbon dioxide as the less soluble component as well as with hydrogen sulfide and carbon sulfide as the more soluble components is withdrawn from the sump of separator 14; this scrubbing methanol now represents the first stream of scrubbing liquid.

The proportion of scrubbing methanol merely preliminarily loaded with carbon dioxide, which is not returned into the column via conduit 9, is expanded in an expansion valve 10 likewise to a pressure of 25 bar. From the head of a phase separator 11 a resultant gaseous phase is withdrawn and combined with the head fraction of phase separator 14. Via conduit 15, 957 Nm$^3$/h. in total of a gaseous mixture is returned, containing 642 Nm$^3$/h. of hydrogen, 265 Nm$^3$/h of carbon dioxide, 30 Nm$^3$/h. of carbon monoxide, argon, and methane as well as 18 Nm$^3$/h. of nitrogen. Of course, the proportion of the dissolved gases flashed off in separators 11 and 14 depends upon the degree of pressure reduction in expansion valves 10 and 13, respectively.

The amount of scrubbing methanol introduced into phase separator 11 is 55 t./h., entraining 13,964 Nm$^3$/h. of dissolved gases. A scrubbing methanol loaded predominantly with carbon dioxide is discharged from the sump of phase separator 11; this scrubbing methanol represents the second stream of scrubbing liquid.

The first as well as the second scrubbing liquid streams are fed via conduits 18 and 17, respectively, to expansion valves 20 and 19, respectively, and expanded therein to a pressure of 3 bar. Both streams are introduced into an enrichment column 21, the first scrubbing liquid stream being fed into the middle section, the second scrubbing liquid stream being fed into the head section provided with a separator. During expansion in the expansion valves 20 and 19, respectively, gaseous fractions are liberated in each case, namely from the second scrubbing liquid stream a fraction consisting primarily of carbon dioxide, discharged from the column overhead, and from the first scrubbing liquid stream a fraction containing carbon dioxide as well as hydrogen sulfide and carbonyl sulfide, this latter fraction rising upwardly in the interior of the column. The proportions of hydrogen sulfide and carbonyl sulfide are rewashed out of this rising gaseous fraction by a part of the second scrubbing liquid stream, this part being returned from the separator at the columm head via a conduit 22 into the upper part of the enrichment column 21. This portion of the second scrubbing liquid stream amounts to 35 t./h. The scrubbing liquid streams accumulating above a flue plate in the lower portion of the enrichment column 21 are withdrawn via a conduit 24, conveyed through heat exchangers 26 and 6 with the aid of a liquid pump 25, and thereafter returned via a conduit 23 into the lowermost part of the enrichment column, which merely functions as a phase separator. During this procedure, the scrubbing liquid streams are warmed from 218 K to 230 K in indirect heat exchange with regenerated scrubbing methanol fed via a conduit 41 and then to 240 K in heat exchange with scrubbing methanol, preliminarily loaded with carbon dioxide and giving off its heat of absorption.

The gaseous fraction liberated by the warming step, which, in turn, contains mostly carbon dioxide, but also hydrogen sulfide and carbonyl sulfide, flows through the flue plate of the enrichment column 21 in the upward direction and during this step is likewise freed, by gas-liquid contact with the second scrubbing liquid stream, of the two sulfur-containing, gaseous components. Additionally, 5,191 Nm$^3$/h. of a gaseous mixture is introduced via a conduit 46 above the sump of the enrichment column 21, this gaseous mixture containing 4,896 Nm$^3$/h. of carbon dioxide and 295 Nm$^3$/h. of hydrogen sulfide and carbonyl sulfide. From the head of the enrichment column 21, 23,316 Nm$^3$/h. of a first product gas is discharged via a conduit 27; this product gas comprises 23,000 Nm$^3$/h. of carbon dioxide, 247 Nm$^3$/h. of hydrogen, and 49 Nm$^3$/h. of carbon monoxide, argon, and methane, as well as 20 Nm$^3$/h. of nitrogen. The purity of this gaseous carbon dioxide product is, therefore, about 98.8 vol.-%. This product gas is obtained at a temperature of 224 K.

From the sump of the enrichment column 21, there is withdrawn 100 t./h. of scrubbing methanol, consisting of the combined first and second scrubbing liquid streams and presently enriched in hydrogen sulfide and carbonyl sulfide. This scrubbing methanol is entraining 7,232 Nm$^3$/h. of carbon dioxide as well as 1,025 Nm$^3$/h. of hydrogen sulfide and carbonyl sulfide, in dissolved form, is fed via a conduit 28 to an expansion valve 42, expanded therein to a pressure of 0.7 bar, and introduced into a phase separator 43. From the phase separator 43, there is passed a gaseous fraction consisting of 4,896 Nm$^3$/h. of carbon dioxide and 295 Nm$^3$/h. of hydrogen sulfide and carbonyl sulfide, to a compressor 44, where the gas is recompressed therein to approximately the pressure of the enrichment column, is then cooled by external cold in a cooler 45, and finally returned via conduit 46 into the enrichment column, to be subjected therein to treatment with the second scrubbing liquid stream.

By means of a liquid pump 29, 100 t./h. of scrubbing liquid containing 2,336 Nm$^3$/h. of carbon dioxide as well as 730 Nm$^3$/h. of hydrogen sulfide and carbonyl sulfide is withdrawn from the sump of separator 43. This amount of scrubbing liquid is fed into a stripping column 30 and conducted in the lower portion thereof in gas-liquid contact with a stripping gas introduced in an amount of 3,000 Nm$^3$/h. via a conduit 31 above the sump of the column. The stripping gas is nitrogen. During this stripping step, 1,486 Nm$^3$/h. of carbon dioxide as well as 103 Nm$^3$/h. of hydrogen sulfide and carbonyl sulfide transfer into the gaseous phase. The thus-loaded stripping gas enters the upper section of the stripping column 30 through a flue plate arranged approximately in the middle of this column, and is freed at that point from the two sulfur-containing components. This is accomplished by means of a partial stream consisting of methanol loaded merely preliminarily with carbon dioxide; this stream is introduced at the head of the column and has previously been branched off from the second scrubbing liquid stream and expanded to a pressure of 1.8 bar in an expansion valve 32. The amount of this partial stream is 20 t./h. The partial stream, now entraining 1,878 Nm$^3$/h. of carbon dioxide as well as 103 Nm$^3$/h. of hydrogen sulfide and carbonyl sulfide, is withdrawn from the stripping column above the flue plate, pressurized by a liquid pump 35 to the pressure of the enrichment column 21, and introduced into the latter. From the head of the stripping column 5,653 Nm$^3$/h. of loaded stripping gas is discharged via a conduit 33. This stripping gas consists of 2,955 Nm$^3$/h. of nitrogen and 2,698 Nm$^3$/h. of carbon dioxide. This loaded stripping gas is obtained under a pressure of 1.8 bar. In the lower section of the stripping column 30, where the actual stripping process takes place, the pressure is 2 bar. From the sump of the stripping column, 100 t./h. of scrubbing methanol greatly enriched with the sulfur-containing components is withdrawn via a conduit 36, namely with the aid of a liquid pump 37. This scrubbing methanol, entraining 1,517 Nm$^3$/h. of dissolved gases, is completely freed of the dissolved gases in a conventional thermal regenerating stage 38 so that a second product gas can be discharged via a conduit 39 consisting of 850 Nm$^3$/h. of carbon dioxide, 627 Nm$^3$/h. of hydrogen sulfide and carbonyl sulfide, 38 Nm$^3$/h. of nitrogen, as well as 2 Nm$^3$/h. of hydrogen. The completely regenerated scrubbing methanol is returned via a liquid pump 40 and by way of conduit 41 to the head of the scrubbing column 2.

The carbon dioxide yield shows the following result in the case of the present example: In the first product gas withdrawn via conduit 27, 86.6% of the carbon dioxide fed with the raw gas is recovered, at a purity of 98.7 vol-%. In the loaded stripping gas withdrawn via conduit 33, 10.2% of the introduced carbon dioxide is contained, whereas in the second product gas discharged via conduit 39, there remains merely 3.2% of the carbon dioxide. The corresponding values in the conventional process of DAS 2,548,700 are 71.4% (98.4 mol-%), about 24.3%, as well as 4.23%. Thus, a considerable improvement can be observed with respect to the product gas yield based on carbon dioxide. The same holds true with respect to the enrichment of the sulfur-containing components hydrogen sulfide and carbonyl sulfide in the second product gas: Thus, in the process of the above example, the concentration ratio between carbon dioxide and the two sulfur-containing components in the raw gas is 42.3; in the second product gas, 1.356, corresponding to an increase in concentration by a factor of 31.2. The corresponding numerical values for the process of DAS 2,548,700 are 31.2; 1.378; and 23.3. Accordingly, even with respect to the increase in concentration in the second product gas, the use of the process of this invention affords a considerable improvement.

It has been assumed in the above example that a sufficient quantity of stripping gas is available. However, the invention is applicable even if this is not the case. Initially, the concentration of the two sulfur-containing components in the sump liquid of separator 43 will still be unsatisfactory, it is true, since it is merely 21.1%, based on the entire amount of carbon dioxide, hydrogen sulfide, and carbonyl sulfide dissolved in the liquid. Such a concentration, though, is inadequate for the further processing of the second product gas in a Claus plant, since in the latter, for reasons of economy, at least 25% of hydrogen sulfide proportion is required as a rule. However, the concentration of the sulfur-containing components in the sump liquid of separator 43 or in the second product gas can be favorably affected by conducting the expansion in the expansion valve 42 to even lower pressures.

Thus, a lowering of the pressure to 0.48 bar is already sufficient to increase the concentration of the sulfur-containing components to 25.4%. Such a lowering of the pressure now will lead to the degasification of 5,396 Nm$^3$/h. instead of 4,896 Nm$^3$/h. of carbon dioxide and 376 Nm$^3$/h. instead of 295 Nm$^3$/h. of hydrogen sulfide and carbonyl sulfide. The proportion of dissolved carbon dioxide in the sump liquid of separator 43 is thus reduced to 1,836 Nm$^3$/h. whereas the proportion of sulfur-containing components recedes to 627 Nm$^3$/h. corresponding to a concentration of 25.4%. This effect can be still further increased by a further lowering of the pressure.

The last-described version of the process exhibits several advantages: No stripping gas is required; the stripping column is eliminated; the carbon dioxide yield is substantially increased since no carbon dioxide is lost with the stripping gas; and the entire second scrubbing liquid stream can be introduced into the head of the enrichment column, i.e. the number of actual plates or the amount of packing material can be reduced, with the purity of the first product gas withdrawn from the head of the enrichment column via conduit 27 remaining the same.

Figure 2:
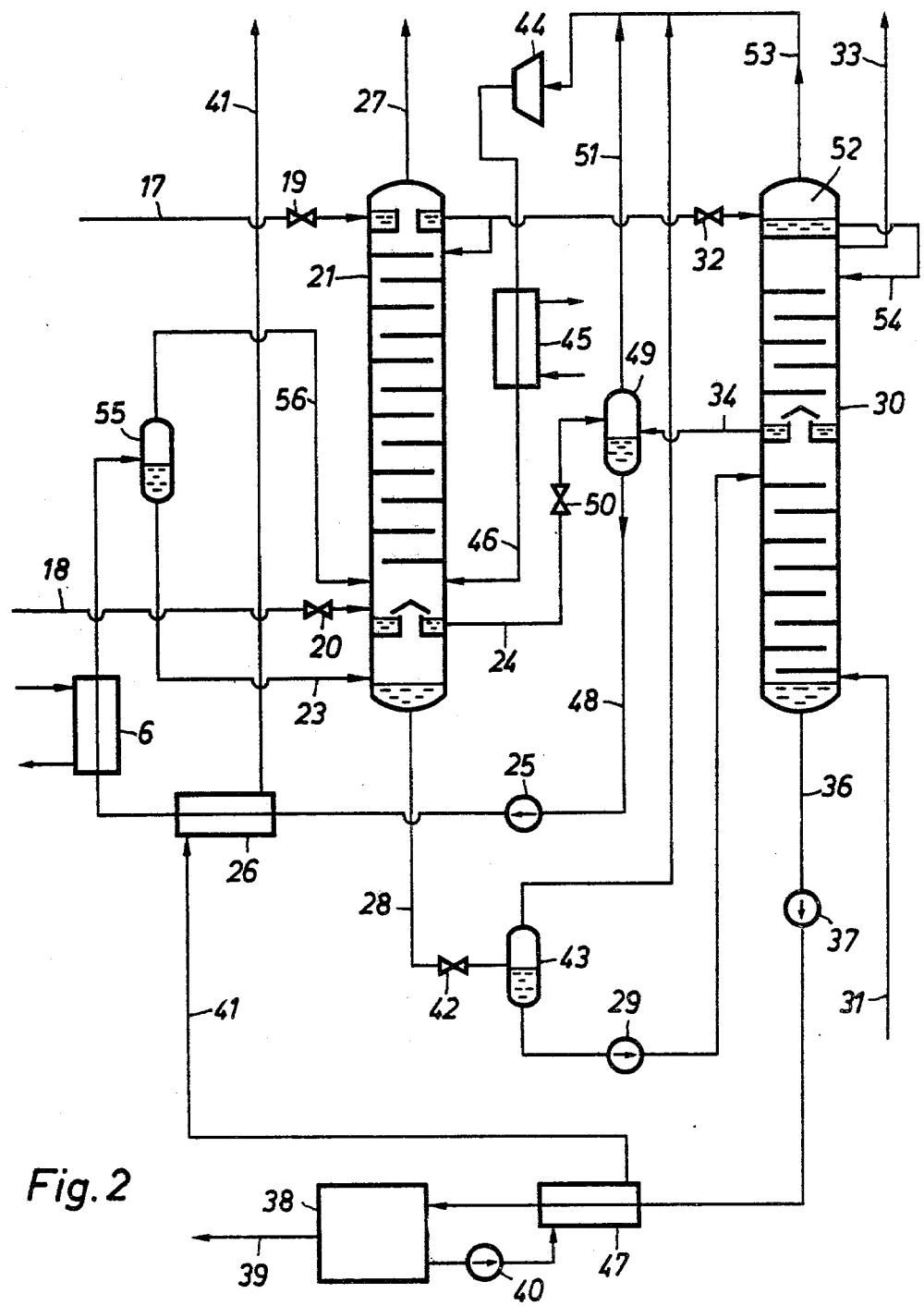
FIG. 2 is a schematic flowsheet of a process embodying still additional possibilities for improvement within the scope of the invention.

The additional example of the invention shown in FIG. 2 demonstrates additional possibilities for increasing efficiency, as mentioned above.

FIG. 2 is adapted to FIG. 1 insofar as identical parts of the apparatus bear identical reference numerals. The left-hand portion of FIG. 1 was omitted from FIG. 2, especially the scrubbing column 2, as well as the separators 11 and 14 with the associated conduits, including the conduits 1 and 3 for the raw gas and the purified gas, respectively.

The above-mentioned additional possibilities reside in conducting an intermediate expansion of the combined two scrubbing liquid streams withdrawn via conduit 24 from the enrichment column 21, effected in an expansion valve 50; conducting, in a separator 55, the liberation of a further gaseous fraction from the scrubbing liquid remaining after the intermediate expansion on account of a preceding heating step; as well as effecting a separate production of a gaseous carbon dioxide fraction after the expansion of the partial stream of scrubbing liquid to be introduced into the stripping column 30, this step taking place in a separator 52.

In this way, the combined scrubbing liquid streams withdrawn above the flue plate of the enrichment column 21 via conduit 24 can be brought, in an expansion valve 50, to an intermediate pressure and can be introduced into the separator 49. The gaseous fraction liberated after this intermediate expansion, which fraction contains carbon dioxide as well as smaller proportions of the two sulfur-containing components, is fed via a conduit 51 to the compressor 44, to be subsequently subjected in the enrichment column likewise to a rewashing of the sulfur-containing components. It is advantageous to effect an intermediate expansion to the pressure ambient above the flue bottom of the stripping column 30, since the scrubbing liquid withdrawn therefrom via conduit 34 can then be conveyed without recompression by means of a liquid pump into the phase separator 49. The sump liquid of the separator 49 is then withdrawn via conduit 48 by means of the liquid pump 25 and recompressed, and furthermore subjected to a dual heating step in heat exchanger 26 and 6, before being returned via conduit 23 into the lower portion of the enrichment column 21, which lower portion functions merely as a separator. Heating takes place in heat exchanger 26 against regenerated scrubbing methanol to be cooled, and in heat exchanger 6 against scrubbing methanol, preliminarily loaded with carbon dioxide from the upper section of the scrubbing column 2. In separator 55, a gaseous fraction is separated containing carbon dioxide, hydrogen sulfide, as well as carbonyl sulfide, and introduced via conduit 56 into the enrichment column 21.

The partial stream of the second scrubbing liquid stream, serving for the re-scrubbing of sulfur-containing components out of the stripping gas and expanded in expansion valve 32, is fed into a phase separator 52 provided at the top of the stripping column. In this separator, a gaseous fraction containing primarily carbon dioxide is separated and likewise fed to compressor 44 via a conduit 53. Thereby almost pure carbon dioxide is additionally obtained. Actually it is unnecessary to subject this fraction to the treatment in the enrichment column, since this fraction is free of sulfur compounds. However, it may be expedient to concomitantly compress this fraction in compressor 44 and thus bring same to the pressure of the first product gas to be withdrawn via conduit 27. The thus-concentrated partial stream is withdrawn from separator 52 via a conduit 54 and introduced into the upper section of the stripping column 30 where it serves for the rewashing of the sulfur-containing components out of the stripping gas. The scrubbing liquid completely regenerated in the warm regenerating stage 38 is customarily subjected to a first cooling step in a heat exchanger 47 against the still loaded scrubbing liquid fed via conduit 36.

As can be seen from the above, the process of this invention can be utilized in the separation and obtaining of sour gases from gaseous mixtures containing same. In this connection, of special interest are carbon dioxide, as the less soluble component and hydrogen sulfide as well as carbonyl sulfide as the more soluble components, since the separation and obtaining of such impurities from raw gases is a problem which occurs with particular frequency. Such raw gases include, for example, coal gasification gases, or gases formed by the partial oxidation of liquid or gaseous hydrocarbons, especially after conversion of the carbon monoxide proportions into carbon dioxide. In this way it is possible for example, to obtain pure hydrogen. However, the invention is nowise limited to this aspect.

Thus, it is possible to utilize the invention, for example, in the purification of natural gas, where the separation of carbon dioxide and hydrogen sulfide is likewise the objective. The ratio of the latter to the former is in this case generally higher than in case of the gases evolving from the carbon monoxide conversion process, and thus the emphasis of the process operation is placed more heavily on the hydrogen sulfide concentration in the second product gas than on the production of the carbon dioxide as the first product gas.

The invention is quite generally applicable to a mixture of at least three gaseous components, wherein it is a prerequisite that a scrubbing liquid is available capable of absorbing at least two of the components with sufficient selectivity with respect to at least one third component, and that, within the group of these at least two absorbed components, there exist, in turn, markedly differing absorbabilities. The effect of the measure of this invention resides in the nature of the physically effective scrubbing liquids, so that the applicability of the invention is not subject to any restrictions with regard to the type of physical scrubbing liquid. Thus, it is possible to employ as the physically effective scrubbing liquids, in addition to methanol disclosed in the practical examples, also for instance acetone, dimethylformamide and/or N-methylpyrrolidone, or also mixtures of N-methylpyrrolidone and methanol, for example for the washing out and separate production of ethylene and acetylene from gaseous mixtures containing these compounds. The last-mentioned physically active scrubbing liquids all exhibit a selectivity for acetylene which is strongly pronounced with respect to ethylene. Furthermore, the invention could, for example, be utilized in the pressure oil scrubbing process for obtaining gasoline hydrocarbons from natural gas or refinery gases, wherein the lighter gasoline hydrocarbons as the less soluble components are to be separated from the heavier gasoline hydrocarbons as the more soluble components.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for separating and obtaining as product gases at least two gaseous components from a gaseous mixture containing same comprising the following steps:

(a) scrubbing said gaseous mixture with a physical scrubbing liquid exhibiting a higher dissolving power for at least one of the components to be separated than for at least one other of these components;

(b) withdrawing a first scrubbing liquid stream, loaded with all of the components to be separated;

(c) withdrawing a second scrubbing liquid stream, merely containing substantially only proportions of the less soluble component or components;

(d) expanding said first scrubbing liquid stream of step (b) to liberate a gaseous fraction and reduced pressure first scrubbing liquid stream;

(e) expanding said second scrubbing liquid stream of step (c) to obtain reduced pressure second scrubbing liquid stream and a gaseous stream containing less soluble component or components;

(f) scrubbing the gaseous fraction of step (d) with the reduced pressure second scrubbing liquid stream of step (e) to remove from said gaseous fraction the more soluble component or components and withdrawing resultant gaseous fraction as a first product stream; and (g) subjecting combined reduced pressure scrubbing liquid streams to a separation of a gas comprising the more soluble components as well as of residual proportions of the less soluble components and withdrawing said gas as a second product gas, the improvement which comprises:

(h) prior to the separation of step (g), further expanding the combined reduced pressure scrubbing liquid streams to obtain a gaseous fraction and a liquid fraction, and separating said gaseous fraction from said liquid fraction;

(i) recompressing the liberated gaseous fraction of step (h);

(j) scrubbing the recompressed gaseous fraction of step (i) with the reduced pressure second scrubbing liquid stream of step (e); and wherein the raw gas contains carbon dioxide as the less soluble component and hydrogen sulfide and/or carbonyl sulfide as the more soluble components.

2. A process according to claim 1, wherein the reduced pressure scrubbing liquid streams, prior to the further expansion, are subjected to an intermediate expansion and are recompressed.

3. A process according to claim 2, wherein the gaseous fraction liberated during the intermediate expansion is recompressed and likewise subjected to scrubbing with the reduced pressure second scrubbing liquid stream.

4. A process according to claim 3, wherein the reduced pressure scrubbing liquid streams are warmed up after intermediate expansion and recompression.

5. A process according to claim 4, wherein the gaseous fraction liberated during the warming-up step is likewise subjected to scrubbing with the reduced pressure second scrubbing liquid stream.

6. A process according to claim 1, wherein the further expanded reduced pressure scrubbing liquid streams are stripped with an inert gas; resultant stripping gas, loaded with thus-liberated components, is treated with a further expanded partial stream branched off from the reduced pressure second scrubbing liquid stream; and the resultant stripped scrubbing liquid streams are subsequently fed to the separating step (g) for obtaining the second product gas.

7. A process according to claim 6, wherein the further expanded partial stream, after the treatment of the loaded stripping gas, is combined with the intermediately expanded, not yet recompressed reduced pressure scrubbing liquid streams.

8. A process according to claim 7, wherein gaseous fraction liberated during the expansion of the partial stream is likewise recompressed and subjected to the treatment with the reduced pressure second scrubbing liquid stream.

9. A process accordng to claim 1, wherein the desired concentration ratio of the more soluble component to the less soluble components in the second product gas is adjusted by influencing the final pressure of the further expansion of the combined reduced pressure scrubbing liquid streams.

10. A process according to claim 1, wherein the scrubbing liquid is methanol.

11. A process according to claim 1, wherein step (g) is a thermal regeneration step.

* * * * *